United States Patent [19]

Gurske

[11] 4,246,084
[45] Jan. 20, 1981

[54] ELECTROPHORETIC TECHNIQUE FOR ASSAYING THE RELATIVE DISTRIBUTION OF LACTATE DEHYDROGENASE ISOENZTIMES AND BUFFERS FOR USE THEREIN

[75] Inventor: William A. Gurske, Placentia, Calif.

[73] Assignee: Beckman Instruments, Inc., Fullerton, Calif.

[21] Appl. No.: 42,845

[22] Filed: May 29, 1979

[51] Int. Cl.$^3$ .................. G01N 33/16; G01N 27/26
[52] U.S. Cl. ......................... 204/180 G; 204/180 S; 204/299 R; 424/12; 23/230 B; 435/26
[58] Field of Search .......... 204/180 R, 180 S, 180 G, 204/299 R; 424/2, 12; 23/230 B; 196/66 R; 195/103.5 R

[56] References Cited

U.S. PATENT DOCUMENTS

| | | | |
|---|---|---|---|
| 2,555,487 | 6/1951 | Haugaard et al. | 204/180 R |
| 3,384,564 | 5/1968 | Ornstein et al. | 204/180 G |
| 3,582,490 | 6/1971 | Zemel | 204/180 G |
| 3,692,654 | 9/1972 | Svendsen | 204/180 R |
| 4,013,513 | 3/1977 | Lederer | 196/66 R |
| 4,139,440 | 2/1979 | Chrambach et al. | 204/180 G |
| 4,147,606 | 4/1979 | Golias | 204/180 G |

OTHER PUBLICATIONS

Buhl et al., "A Search for the Best Buffer . . . . . ", Clin. Chem., 22(11): 1872–1875 (1976).
Gueffroy, Ed., "A Guide for the Preparation and Use of Buffers in Biological System", Calbiochem, LaJolla, CA. (1975).

Primary Examiner—Arthur C. Prescott
Attorney, Agent, or Firm—R. J. Steinmeyer; Robert R. Meads; Robert S. Frieman

[57] ABSTRACT

An electrophoretic technique for assaying the relative distribution of lactate dehydrogenase (LD) isoenzymes characterized in that the electrophoretic and/or substrate buffer employed therein comprises a first and second moiety wherein the first moiety is selected from a group consisting of alkali metal 5,5-diethylbarbiturate, ammonium 5,5-diethylbarbiturate, and mixtures thereof, and wherein the second moiety is selected from a group consisting of bicine (N,N-bis(2-hydroxyethyl)glycine), tricine (N-tris(hydroxymethyl)methylglycine), and glycylglycine. The buffer has a pH of from about 7 to about 9 at 25° C.

Preferably, the buffer further comprises a solid organic water soluble acid and either 2-amino-2-methyl-1,3-propanediol (AMPD) or 2-amino-2-hydroxymethyl-1,3-propanediol (Tris) or mixtures thereof.

Buffers within the scope of the instant invention, when compared to prior art buffers, increase the relative percentage of $LD_5$ and thereby improve the accuracy and reproducibility of the electrophoretic data.

15 Claims, No Drawings

ELECTROPHORETIC TECHNIQUE FOR ASSAYING THE RELATIVE DISTRIBUTION OF LACTATE DEHYDROGENASE ISOENZYMES AND BUFFERS FOR USE THEREIN

BACKGROUND OF THE INVENTION

1. Field of the Invention

The instant invention pertains to an electrophoretic technique for assaying the relative distribution of LD isoenzymes and to a buffer for use therein.

2. Description of the Prior Art

LD isoenzymes are distributed in all tissues of the human body. Serum contains five isoenzymes of LD. It has been shown that diseases affecting body tissues will often cause a change in the relative distribution of the LD isoenzymes occurring in serum. Therefore, by measuring the relative distribution of LD isoenzymes in serum, one can obtain diagnostic information on an individual.

The general analysis of isoenzymes, including LD isoenzymes, is usually performed by an electrophoretic technique. The electrophoretic technique can be broken down into three basic steps. Step 1 is the physical separation of the enzyme into its various isoenzyme components. In general, the electrophoretic separation of isoenzymes is accomplished by applying a sample, such as human serum, to a buffered electrophoretic medium. (Conventional electrophoretic mediums include, but are not limited to, gels, e.g., polyacrylamide and agarose, and membranes, e.g., cellulose acetate and cellulose.) The buffered electrophoretic medium is placed into a chamber known as an electrophoretic cell which contains an aqueous buffer known as an electrophoretic buffer. (The buffer employed to buffer the electrophoretic medium can be the same or different from the buffer employed as the electrophoretic buffer.) The buffered electrophoretic medium is placed in direct contact with the electrophoretic buffer and in turn the electrophoretic buffer is in direct contact with two separate electrodes (a cathode and an anode). The electrodes are connected with a direct current power source whereby the electrophoretic process takes place when direct current is applied to the electrophoretic medium. In order to adequately separate the various isoenzyme constituents, the electrophoretic process usually takes place at an established electrical potential, for example, from about 50 to about 500 volts, and for a sufficient length of time, for example, from about 0.1 to about 2 hours.

Step 2 is the detection of each isoenzyme component. This consists of a set of chemical reactions wherein each set of reactions is catalyzed by one of the isoenzymes to produce a corresponding, detectable chemical product, such as a colored or fluorescent product. The detection of each isoenzyme component requires contacting the separated isoenzymes with reagents capable of reacting to produce a detectable product. One method well known to those skilled in the art encompasses contacting the separated isoenzymes with a substrate solution containing said reagents. The substrate solution can be either applied directly or the surface of the electrophoretic medium or can be first incorporated into a stabilizing medium, such as filter paper, chromatography paper, cellulose acetate membrane, agarose gel, etc., and then applied to the surface of the electrophoretic medium. The substrate solution generally comprises a substrate buffer, an activator, e.g., metal ions, specific reactants or substrates, and a substance capable of producing a detectable chemical product, e.g., a co-enzyme, i.e., NAD, NADP, derivatives thereof, and mixtures thereof, or a dye capable of forming a colored pigment.

After electrophoresis, the electrophoretic medium is removed from the electrophoretic cell and is placed into an incubation chamber. The substrate solution is applied to the surface of the electrophoretic medium and the electrophoretic medium is then incubated at a predetermined temperature and for a predetermined time.

Step 3 is a quantitation of each isoenzyme component. This is accomplished by scanning either the electrophoretic medium or the substrate medium with a suitable detection means, e.g., fluorometer or densitometer, to quantitate the chemical product produced by each isoenzyme component. The amount and position of each product detected is proportional to its corresponding isoenzyme located in the electrophoretic medium.

The electrophoretic buffer employed in the first part of the above electrophoretic process controls the electrophoretic separation of the isoenzymes while the substrate buffer employed in the second part of the electrophoretic process controls the pH of the substrate solution and thus the chemical activity of each isoenzyme.

In prior art analyses of LD isoenzymes, a barbital buffer having a pH of from about 8 to about 9 is generally employed in the first part of the electrophoretic procedure for the separation of the LD isoenzymes. In the second portion of the prior art electrophoresis procedures, the buffer employed in the substrate solution for LD isoenzyme analysis varies considerably with each author and commercial method. This may be due to the general belief that if barbital buffer is employed for the substrate solution, a reduction in the relative percentage of $LD_5$ isoenzymes will occur. See Rosalki, *Clin. Biochem.*, 7:29–40 (1974), said publication being incorporated herein in toto by reference.

SUMMARY OF THE INVENTION

The instant invention encompasses an improved electrophoretic technique for assaying the relative distribution of LD isoenzymes. The electrophoretic technique is of the type wherein a sample containing LD is applied to a buffered electrophoretic medium, the buffered electrophoretic medium is placed into an electrophoretic cell having located therein an electrophoretic buffer in contact with two electrodes, a direct electric current is applied to the electrophoretic medium whereby LD is separated into its constituent isoenzymes, a substrate solution comprising a substrate buffer, an activator, a substrate, and a substance capable of producing a detectable chemical product, is applied to the electrophoretic medium containing the separated LD isoenzymes whereby the isoenzymes react quantitatively to produce a detectable product at their location in the electrophoretic medium, and the amount and location of each detectable product is measured, thereby quantitating the relative distribution of LD isoenzymes in the sample being assayed. The improved electrophoretic technique of the instant invention is characterized in that the electrophoretic buffer and/or the substrate solution buffer comprises a first and second moeity wherein the first moeity is selected from a group consisting of alkali metal 5,5-diethylbarbiturate, ammonium 5,5-diethylbarbiturate, and mixtures thereof, and wherein the second moeity is selected from a group consisting of bicine (N,N-bis(2-hydroxyethyl)glycine), tricine (N-tris(hydroxymethyl)methylglycine), and glycylglycine, the buffer having a pH of from about 7 to about 9 at 25° C.

It is preferred that the buffer of the instant invention further comprise a solid organic water soluble acid and either AMPD (2-amino-2-methyl-1,3-propanediol) or Tris (2-amino-2-hydroxymethyl-1,3-propanediol) or mixtures thereof.

Buffers within the scope of the instant invention, when compared to a prior art buffer, increase the relative percentage of $LD_5$ and thereby improve the accuracy and reproducibility of the electrophoretic data.

DESCRIPTION OF THE PREFERRED EMBODIMENTS

The electrophoretic and/or substrate buffer employed in this invention's electrophoretic technique for assaying the relative distribution of LD isoenzymes comprises a first and second moiety wherein the first moiety is selected from a group consisting of alkali metal 5,5-diethylbarbiturate, ammonium 5,5-diethylbarbiturate, and mixtures thereof, and wherein the second moiety is selected from a group consisting of bicine, tricine, and glycylglycine. The buffer has a pH of from about 7 to about 9 at 25° C.

Preferably, the buffer of the instant invention comprises from about 2.5 grams to about 10 grams per liter of the first moiety and from 1 to about 4 grams per liter of the second moiety. More preferably, the buffer of the instant invention comprises about 5 grams per liter of the first moiety and about 2 grams per liter of the second moiety.

The pH range of the buffer of this invention is preferably from about 8 to about 9; more preferably, from about 8 to about 8.5; and optimally from about 8.3 to about 8.4.

The first moiety is preferably selected from the group consisting of sodium 5,5-diethylbarbiturate, lithium 5,5-diethylbarbiturate, and potassium 5,5-diethylbarbiturate, and mixtures. More preferably, the first moiety is sodium 5,5-diethylbarbiturate.

In another embodiment of the invention a solid organic water soluble acid and either AMPD or Tris or mixtures thereof are included in the buffer system. This preferred buffer, when employed in an electrophoretic technique, yields LD peaks having a symmetrical distribution.

The pH range of the buffer of this latter embodiment is preferably from 7.5 to 8.5.

Also, this buffer preferably comprises from about 0.5 to about 10 grams per liter of the first moiety; from about 0.5 to about 10 grams per liter of the second moiety; from about 0.5 to about 10 grams per liter of the solid organic water soluble acid; and from about 0.5 to about 10 grams per liter of a composition selected from a group consisting of AMPD, Tris, and mixtures thereof.

More preferably, this latter buffer system comprises from about 2 to 4 grams per liter of the first moiety; from about 3 to about 5 grams per liter of the second moiety; from about 2 to about 4 grams per liter of the solid organic water soluble acid; and from about 3 to about 5 grams per liter of the composition.

Examples of solid organic water soluble acids include, but are not limited to, maleic acid, malonic acid, fumaric acid, and amino acids such as aspartic acid, glutamic acid, glycine, alanine, valine, leucine, isoleucine, serine, threonine, phenylalanine, and tyrosine.

Preferably the solid organic water soluble acid is selected from a group consisting of maleic acid, malonic acid, fumaric acid, aspartic acid and glutamic acid. More preferably the solid organic water soluble acid is aspartic acid.

Table I, infra, sets forth various preferred buffers within the scope of this instant invention.

TABLE I

| Aspartic Acid | Bicine | Sodium Barbital | AMPD | Tris | pH |
|---|---|---|---|---|---|
| 1.0 | 4.0 | 3.0 | 2.0 | 0 | 8.2 |
| 1.5 | 6.0 | 4.5 | 3.0 | 0 | 8.2 |
| 1.0 | 6.0 | 3.0 | 2.7 | 0 | 8.2 |
| 1.0 | 2.0 | 3.0 | 1.1 | 0 | 8.1 |
| 3.0 | 2.0 | 3.0 | 3.3 | 0 | 8.2 |
| 5.0 | 2.0 | 3.0 | 5.3 | 0 | 8.2 |
| 3.0 | 4.0 | 7.0 | 3.0 | 0 | 8.2 |
| 3.0 | 6.0 | 3.0 | 4.8 | 0 | 8.2 |
| 3.0 | 0.5 | 3.0 | 2.6 | 0 | 8.2 |
| 3.0 | 4.0 | 3.0 | 0 | 7.6 | 8.2 |
| 3.0 | 4.0 | 3.0 | 0 | 5.2 | 8.2 |
| 3.0 | 4.0 | 3.0 | 0 | 4.8 | 7.9 |
| 3.0 | 4.0 | 3.0 | 0 | 4.0 | 7.8 |

The following examples are provided for the purpose of further illustration only and are not intended to be limitations on the disclosed invention.

EXAMPLES 1-6

The following buffers were prepared by dissolving their various constituents in deionized water:

Buffers Within the Scope of this Invention:

1. Barbital-Bicine Buffer
   5.0 gm sodium 5,5-diethylbarbiturate (sodium barbital)
   2.0 gm bicine
   1000 ml deionized water
   pH 8.40
2. Barbital-Tricine Buffer
   5.0 gm sodium barbital
   2.0 gm tricine
   1000 ml deionized water
   pH 8.31
3. Barbital-Glycylglycine Buffer
   5.0 gm sodium barbital
   1.5 gm glycylglycine
   1000 ml deionized water
   pH 8.38

Prior Art Buffer:

4. Barbital Buffer
   5.0 gm sodium barbital
   1.75 gm 5,5-diethylbarbituric acid (acid barbital)
   1000 ml deionized water
   pH 8.32

Other Buffers Outside Scope of this Invention:

5. Barbital-TES Buffer
   5.0 gm sodium barbital
   1.75 gm N-tris(hydroxymethyl)methyl-2-aminoethanesulfonic acid (TES)
   1000 ml deionized water
   pH 8.37
6. Barbital-HEPES
   5.0 gm sodium barbital
   2.25 gm N-2-hydroxyethylpiperazine-N'-2-ethanesulfonic acid (HEPES)
   1000 ml deionized water pH 8.30

EXAMPLES 7-12

Agarose gels (12) having eight sample slots per gel were hydrated overnight in deionized water. Each of the six sets of 2 gels was equilibrated (buffered) with 100 ml of a different one of the six buffers prepared in Examples 1-6 for 15 minutes and then blotted to remove any excess buffer. A single electrophoretic control sample was used. An aliquot (5 μl) of the electrophoretic control sample was applied to each of the eight sample slots on each agarose gel. Each gel was electrophoresed for 30 minutes at 150 volts in an electrophoretic cell containing the same buffer as used in the equilibration step. Each gel was then placed into an incubation tray and submerged in 50 ml of the following substrate solution:

Substrate Solution 200 mg L(+)lactic acid, lithium salt
40 mg nicotinamide adenine dinucleotide
20 mg p-nitro blue tetrazodium chloride
1 mg phenazine methosulfate
50 ml of a buffer prepared in Examples 1-6

The substrate solution employed with each set of 2 gels contained therein a substrate buffer corresponding to the buffer applied to that gel in the equilibration and electrophoretic separation steps.

Each incubation tray having located thereon a gel covered with a particular substrate solution was incubated at 37° C. for 45 minutes. The stained gels were then destained in the dark in a 5% aqueous solution acetic acid solution for 60 minutes. The 5% acetic acid solution was changed after 30 minutes. The destained gels then were dried at 80° C. for 60 minutes. These dried, destained gels were scanned with a densitometer at 600 nm and the relative percentage of each LD isoenzyme is set forth in Tables I-VI for each of the buffers employed. Table VII summarizes the data set forth in Tables I-VI.

TABLE I

BARBITAL-BICINE BUFFER
LDH ISOENZYME

| Sample | I | II | III | IV | V |
|---|---|---|---|---|---|
| Slot | | First Gel | | | |
| 1 | 31.0 | 37.4 | 19.3 | 3.7 | 8.7 |
| 2 | 27.1 | 39.7 | 20.4 | 4.3 | 8.5 |
| 3 | 28.6 | 37.4 | 20.7 | 5.0 | 8.4 |
| 4 | 27.7 | 38.2 | 21.2 | 5.5 | 7.4 |
| 5 | 22.7 | 37.7 | 23.8 | 6.3 | 9.5 |
| 6 | 21.3 | 38.5 | 25.6 | 5.7 | 8.9 |
| 7 | 21.9 | 36.7 | 25.7 | 6.6 | 8.7 |
| 8 | 21.1 | 36.3 | 26.2 | 6.6 | 9.0 |
| | | Second Gel | | | |
| 1 | 20.7 | 41.2 | 24.3 | 4.3 | 8.0 |
| 2 | 19.8 | 44.2 | 24.1 | 4.6 | 6.9 |
| 3 | 20.7 | 40.5 | 25.7 | 5.0 | 8.0 |
| 4 | 21.0 | 39.5 | 28.3 | 4.3 | 6.9 |
| 5 | 19.9 | 36.1 | 27.0 | 6.3 | 10.1 |
| 6 | 19.5 | 37.7 | 27.0 | 4.9 | 10.3 |
| 7 | 20.1 | 36.7 | 27.1 | 5.7 | 10.4 |
| 8 | 19.9 | 34.8 | 26.7 | 6.3 | 11.6 |
| Average: | 22.7 | 37.5 | 24.7 | 5.5 | 9.3 |

TABLE II

BARBITAL-TRICINE BUFFER
LDH ISOENZYME

| Sample | I | II | III | IV | V |
|---|---|---|---|---|---|
| Slot | | First Gel | | | |
| 1 | 24.0 | 40.4 | 23.1 | 3.7 | 8.8 |
| 2 | 21.0 | 39.4 | 24.5 | 5.2 | 9.9 |
| 3 | 23.9 | 38.4 | 23.4 | 5.3 | 9.0 |
| 4 | 24.4 | 39.0 | 23.5 | 4.7 | 8.4 |
| 5 | 20.3 | 35.0 | 25.5 | 7.2 | 12.1 |
| 6 | 20.8 | 35.5 | 25.0 | 6.5 | 11.4 |
| 7 | 20.9 | 35.2 | 25.1 | 6.5 | 11.6 |
| 8 | 20.4 | 33.1 | 25.0 | 8.3 | 12.6 |
| | | Second Gel | | | |
| 1 | 25.1 | 36.9 | 27.2 | 3.8 | 7.0 |
| 2 | 25.4 | 38.4 | 24.0 | 3.8 | 8.4 |
| 3 | 26.7 | 36.8 | 22.9 | 5.1 | 8.6 |
| 4 | 26.0 | 36.8 | 21.8 | 5.6 | 10.7 |
| 5 | 21.9 | 35.1 | 26.2 | 6.3 | 10.3 |
| 6 | 19.9 | 35.2 | 26.6 | 6.1 | 11.1 |
| 7 | 21.8 | 35.7 | 27.0 | 5.7 | 9.7 |
| 8 | 22.6 | 35.8 | 26.5 | 5.7 | 9.1 |
| Average: | 22.8 | 36.7 | 24.8 | 5.6 | 9.9 |

TABLE III

BARBITAL-GLYCYLGLYCINE BUFFER
LDH ISOENZYME

| Sample | I | II | III | IV | V |
|---|---|---|---|---|---|
| Slot | | First Gel | | | |
| 1 | 21.7 | 44.8 | 21.5 | 3.2 | 8.8 |
| 2 | .17.8 | 46.1 | 25.0 | 3.4 | 7.7 |
| 3 | 20.9 | 41.2 | 21.2 | 5.3 | 10.0 |
| 4 | 21.5 | 44.3 | 22.8 | 3.4 | 8.8 |
| 5 | 18.5 | 41.4 | 25.6 | 5.8 | 8.7 |
| 6 | 15.9 | 41.6 | 28.3 | 5.1 | 8.9 |
| 7 | 17.2 | 40.0 | 25.5 | 6.3 | 10.1 |
| 8 | 17.8 | 40.2 | 27.5 | 5.5 | 9.0 |
| | | Second Gel | | | |
| 1 | 20.4 | 46.1 | 23.3 | 2.6 | 7.6 |
| 2 | 20.2 | 48.0 | 21.5 | 2.5 | 7.8 |
| 3 | 21.8 | 45.1 | 22.5 | 2.6 | 8.0 |
| 4 | 20.3 | 46.0 | 22.6 | 3.4 | 7.6 |
| 5 | 17.1 | 36.6 | 28.9 | 5.5 | 10.5 |
| 6 | 14.5 | 28.4 | 21.6 | 11.7 | 23.8 |
| 7 | 17.8 | 39.4 | 26.3 | 5.5 | 9.9 |
| 8 | 18.1 | 40.9 | 25.0 | 5.1 | 10.0 |
| Average: | 18.8 | 41.9 | 24.3 | 4.8 | 9.8 |

TABLE IV

BARBITAL BUFFER
LDH ISOENZYME

| Sample | I | II | III | IV | V |
|---|---|---|---|---|---|
| Slot | | First Gel | | | |
| 1 | 26.3 | 42.2 | 23.1 | 2.6 | 5.8 |
| 2 | 23.5 | 43.6 | 23.4 | 3.3 | 5.8 |
| 3 | 22.7 | 43.1 | 24.3 | 3.4 | 6.5 |
| 4 | 24.4 | 39.8 | 25.7 | 3.7 | 6.4 |
| 5 | 19.7 | 40.3 | 27.9 | 5.2 | 6.9 |
| 6 | 17.5 | 38.7 | 29.3 | 5.1 | 9.0 |
| 7 | 18.7 | 38.8 | 30.6 | 4.2 | 7.7 |
| 8 | 17.7 | 39.9 | 29.1 | 4.9 | 7.8 |
| | | Second Gel | | | |
| 1 | Smear | Smear | Smear | Smear | Smear |
| 2 | Smear | Smear | Smear | Smear | Smear |
| 3 | Smear | Smear | Smear | Smear | Smear |
| 4 | Smear | Smear | Smear | Smear | Smear |
| 5 | 16.8 | 40.0 | 31.7 | 4.5 | 7.0 |
| 6 | 16.1 | 39.9 | 27.7 | 7.1 | 7.9 |
| 7 | 16.5 | 39.3 | 31.5 | 4.5 | 7.4 |
| 8 | 16.3 | 38.5 | 31.9 | 4.4 | 8.1 |
| Average: | 19.7 | 40.3 | 28.0 | 4.4 | 7.2 |

TABLE V

BARBITAL-TES BUFFER LDH ISOENZYME

| Sample | I | II | III | IV | V |
|---|---|---|---|---|---|
| Slot | | First Gel | | | |
| 1 | 21.8 | 40.4 | 29.5 | 3.6 | 4.7 |
| 2 | 19.9 | 41.0 | 30.3 | 3.4 | 5.4 |
| 3 | 21.4 | 41.6 | 29.4 | 3.3 | 4.4 |
| 4 | 23.5 | 40.6 | 28.3 | 3.1 | 4.5 |
| 5 | 20.2 | 39.4 | 30.1 | 4.4 | 5.7 |
| 6 | 19.9 | 40.8 | 29.5 | 3.9 | 5.8 |
| 7 | 19.5 | 38.8 | 29.6 | 4.8 | 7.3 |
| 8 | 18.9 | 38.0 | 30.9 | 5.1 | 7.1 |
| | | Second Gel | | | |
| 1 | 19.8 | 39.8 | 29.0 | 5.0 | 6.5 |
| 2 | 18.2 | 40.3 | 31.1 | 4.9 | 5.4 |
| 3 | 19.1 | 41.9 | 30.1 | 3.9 | 4.9 |
| 4 | 20.4 | 39.4 | 30.1 | 4.8 | 5.3 |
| 5 | 19.2 | 38.2 | 31.1 | 5.4 | 6.0 |
| 6 | 17.8 | 41.0 | 30.2 | 4.7 | 6.2 |
| 7 | 18.2 | 39.1 | 31.0 | 5.1 | 6.6 |
| 8 | 18.2 | 37.2 | 30.0 | 6.3 | 8.1 |
| Average: | 19.8 | 39.8 | 30.0 | 4.5 | 5.9 |

TABLE VI

BARBITAL-HEPES BUFFER LDH ISOENZYME

| Sample | I | II | III | IV | V |
|---|---|---|---|---|---|
| Slot | | First Gel | | | |
| 1 | 24.0 | 38.7 | 30.6 | 3.9 | 2.2 |
| 2 | 25.1 | 36.9 | 30.0 | 3.6 | 3.8 |
| 3 | 25.7 | 38.0 | 30.0 | 3.6 | 2.7 |
| 4 | 26.5 | 38.1 | 30.8 | 2.9 | 1.6 |
| 5 | 22.8 | 40.1 | 30.5 | 4.4 | 1.7 |
| 6 | 23.7 | 39.2 | 30.5 | 4.5 | 2.0 |
| 7 | 23.7 | 37.2 | 29.6 | 5.6 | 3.9 |
| 8 | 23.4 | 37.0 | 30.1 | 5.6 | 3.5 |
| | | Second Gel | | | |
| 1 | 22.8 | 41.9 | 29.2 | 3.1 | 2.9 |
| 2 | 21.1 | 44.1 | 30.9 | 2.6 | 1.1 |
| 3 | 21.8 | 43.3 | 30.9 | 2.6 | 1.4 |
| 4 | 23.4 | 44.0 | 29.8 | 2.3 | 0.5 |
| 5 | 20.7 | 42.4 | 31.5 | 4.2 | 1.3 |
| 6 | 20.4 | 42.1 | 30.9 | 4.4 | 2.2 |
| 7 | 21.3 | 41.5 | 30.8 | 3.7 | 2.5 |
| 8 | 20.0 | 40.7 | 30.8 | 5.1 | 3.0 |
| Average: | 22.9 | 40.3 | 30.4 | 3.9 | 2.3 |

TABLE VII

| Buffer | $LD_1$ | $LD_2$ | $LD_2$ | $LD_4$ | $LD_5$ |
|---|---|---|---|---|---|
| BUFFERS WITHIN SCOPE OF INVENTION | | | | | |
| Barbital-Bicine | 22.7 | 37.5 | 24.7 | 5.5 | 9.3 |
| Barbital-Tricine | 22.8 | 36.7 | 24.8 | 5.6 | 9.9 |
| Barbital-Glyclglycine | 18.8 | 41.9 | 24.3 | 4.8 | 9.8 |
| BUFFERS OUTSIDE SCOPE OF INVENTION | | | | | |
| Barbital | 19.7 | 40.3 | 28.0 | 4.4 | 7.2 |
| Barbital-TES | 19.8 | 39.8 | 30.0 | 4.5 | 5.9 |
| Barbital-HEPES | 22.9 | 40.3 | 30.4 | 3.9 | 2.3 |

Table VII evidences the fact that the buffers within the scope of the instant invention, when compared to the prior art barbital buffer, increase the relative percentage of $LD_5$ and thereby improve the accuracy and reproducibility of the data obtained.

Furthermore, the data obtained using barbital-TES and barbital-HEPES buffers shows that by employing a second moiety comprising a zwitterion buffer having a similar pKa (see Good et al., Biochemistry, 5(2):467–477 (1966)) in conjunction with a barbital buffer one does not as a matter of course increase the relative percentage of $LD_5$ but can in fact decrease $LD_5$'s relative percentage.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A buffer comprising a first and second moeity wherein said first moeity is selected from a group consisting of alkali metal 5,5-diethylbarbiturate, ammonium 5,5-diethylbarbiturate, and mixtures thereof, and wherein said second moeity is selected from a group consisting of bicine, tricine, and glycylglycine, said buffer having a pH of from about 7 to about 9 at 25° C.

2. The buffer of claim 1 comprising from about 2.5 to about 10 grams per liter of said first moiety and from about 1 to about 4 grams per liter of said serum moiety and having a pH of from about 8 to about 9 at 25° C.

3. The buffer of claim 1 wherein said first moiety is selected from the group consisting of sodium 5,5-diethylbarbiturate, lithium 5,5-diethylbarbiturate, potassium 5,5-diethylbarbiturate, and mixtures thereof and wherein said buffer has a pH of from about 8 to about 8.5 at 25° C.

4. The buffer of claim 3 comprising about 5 grams per liter of said first moiety and about 2 grams per liter of said second moiety; wherein said first moiety is sodium 5,5-diethylbarbiturate; wherein said second moiety is selected from the group consisting of bicine and tricine; and wherein said buffer has a pH of from about 8.3 to about 8.4 at 25° C.

5. The buffer of claim 1 further comprising a solid organic water soluble acid and a composition selected from a group consisting of 2-amino-2-methyl-1,3-propanedial, 2-amino-2-hydroxymethyl-1,3-propandiol, and mixtures thereof.

6. The buffer of claim 5 comprising:
(a) from about 0.5 to about 10 grams per liter of said first moiety;
(b) from about 0.5 to about 10 grams per liter of said second moiety;
(c) from about 0.5 to about 10 grams per liter of said solid organic water soluble acid; and
(d) from about 0.5 to about 10 grams per liter of said composition.

7. The buffer of claim 6 wherein:
(a) said first moiety is selected from the group consisting of sodium 5,5-diethylbarbiturate, lithium 5,5-diethylbarbiturate, potassium 5,5-diethylbarbiturate, and mixtures thereof;
(b) said second moiety is selected from the group consisting of bicine and tricine; and
(c) said solid organic water soluble acid is selected from a group consisting of amino acids, maleic acid, malonic acid, and fumaric acid.

8. The buffer of claim 7 comprising:
(a) from about 2 to about 4 grams per liter of sodium 5,5-diethylbarbiturate;
(b) from about 3 to about 5 grams per liter of said second moiety;
(c) from about 2 to about 4 grams per liter of aspartic acid; and
(d) from about 3 to about 5 grams per liter of said composition; and
having a pH of about 7.5 to about 8.5 at 25° C.

9. The buffer of claim 8 comprising:

(a) about 3 grams per liter of sodium 5,5-diethylbarbiturate;
(b) about 4 grams per liter of bicine;
(c) about 3 grams per liter of aspartic acid; and
(d) about 4 grams per liter of said composition selected from the group consisting of 2-amino-2-methyl-1,3-propanodial and 2-amino-2-hydroxymethyl-1,3-propanediol.

10. An improved electrophoretic technique for assaying the relative distribution of lactate dehydrogenase isoenzymes of the type wherein a sample to be assayed is applied to a buffered electrophoretic medium, said buffered electrophoretic medium is placed into an electrophoretic cell having located therein an electrophoretic buffer, lactate dehydrogenase present in said sample is separated into its constituent isoenzymes, a substrate solution, comprising a substrate buffer, an activator, a substrate, and a substance capable of producing a detectable chemical product, is applied to the electrophoretic medium containing said separated isoenzymes whereby the isoenzymes react quantitively to produce a detectable product at their location in the electrophoretic medium, and the amount and location of each detectable product is measured, thereby quantitating the relative distribution of lactate dehydrogenase isoenzymes in the sample being assayed, wherein the improvement comprises using the buffer of any one of claims 1-8 or 9 as said electrophoretic buffer.

11. An improved electrophoretic technique for assaying the relative distribution of lactate dehydrogenase isoenzymes of the type wherein a sample to be assayed is applied to a buffered electrophoretic medium, said buffered electrophoretic medium is placed into an electrophoretic cell having located therein an electrophoretic buffer, lactate dehydrogenase present in said sample is separated into its constituent isoenzymes, a substrate solution, comprising a substrate buffer, an activator, a substrate, and a substance capable of producing a detectable chemical product, is applied to the electrophoretic medium containing said separated isoenzymes whereby the isoenzymes react quantitively to produce a detectable product at their location in the electrophoretic medium, and the amount and location of each detectable product is measured, thereby quantitating the relative distribution of lactate dehydrogenase isoenzymes in the sample being assayed, wherein the improvement comprises using the buffer of any one of claims 1-8 or 9 as said substrate buffer.

12. An improved electrophoretic technique for assaying the relative distribution of lactate dehydrogenase isoenzymes of the type wherein a sample to be assayed is applied to a buffered electrophoretic medium, said buffered electrophoretic medium is placed into an electrophoretic cell having located therein an electrophoretic buffer, lactate dehydrogenase present in said sample is separated into its constituent isoenzymes, a substrate solution, comprising a substrate buffer, an activator, a substrate, and a substance capable of producing a detectable chemical product, is applied to the electrophoretic medium containing said separated isoenzymes whereby the isoenzymes react quantitively to produce a detectable product at their location in the electrophoretic medium, and the amount and location of each detectable product is measured, thereby quantitating the relative distribution of lactate dehydrogenase isoenzymes in the sample being assayed, wherein the improvement comprises using the buffer of any one of claims 1-8 or 9 as said electrophoretic and substrate buffers.

13. An improved electrophoretic technique for assaying the relative distribution of lactate dehydrogenase isoenzymes of the type wherein a sample to be assayed is applied to a buffered electrophoretic medium, said buffered electrophoretic medium is placed into an electrophoretic cell having located therein an electrophoretic buffer, lactate dehydrogenase present in said sample is separated into its constituent isoenzymes, a substrate solution, comprising a substrate buffer, an activator, a substrate, and a substance capable of producing a detectable chemical product, is applied to the electrophoretic medium containing said separated isoenzymes whereby the isoenzymes react quantitively to produce a detectable product at their location in the electrophoretic medium, and the amount and location of each detectable product is measured, thereby quantitating the relative distribution of lactate dehydrogenase isoenzymes in the sample being assayed, wherein the improvement comprises using the buffer of any one of claims 1-8 or 9 as said electrophoretic and substrate buffers and to buffer the electrophoretic medium.

14. A substrate solution of the type comprising a substrate buffer, an activator, a substrate, and a substance capable of producing a detectable chemical product, characterized in that said substrate buffer is the buffer of any one of claims 1-8 or 9.

15. A buffered electrophoretic medium of the type comprising an electrophoretic medium and a buffer, characterized in that said buffer is the buffer of any one of claims 1-8 or 9.

* * * * *